US008423120B2

(12) United States Patent
Tynes et al.

(10) Patent No.: US 8,423,120 B2
(45) Date of Patent: Apr. 16, 2013

(54) METHOD AND APPARATUS FOR POSITIONING A BIOPSY NEEDLE

(75) Inventors: Thomas E. Tynes, Mukwonago, WI (US); Bernd Kümmerlen, Bremen (DE); Jens Breitenborn, Bremen (DE); Hartmut Jürgens, Bremen (DE); Sven Kohle, Bremen (DE); Jessica Brandt, Zeven (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1629 days.

(21) Appl. No.: 11/199,768

(22) Filed: Aug. 8, 2005

(65) Prior Publication Data
US 2006/0052693 A1 Mar. 9, 2006

Related U.S. Application Data

(60) Provisional application No. 60/600,190, filed on Aug. 6, 2004.

(51) Int. Cl.
*A61B 5/05* (2006.01)
(52) U.S. Cl.
USPC ........... 600/424; 600/415; 600/425; 600/437; 600/476; 382/128
(58) Field of Classification Search .................. 600/407, 600/415, 425, 437, 476; 382/128, 130, 131
See application file for complete search history.

(56) References Cited

U.S. PATENT DOCUMENTS

| | | | |
|---|---|---|---|
| 6,138,045 A * | 10/2000 | Kupinski et al. | 600/425 |
| 7,379,769 B2 * | 5/2008 | Piron et al. | 600/415 |
| 2001/0032649 A1 | 10/2001 | Nagano | |
| 2002/0131625 A1 * | 9/2002 | Vining et al. | 382/128 |
| 2003/0220559 A1 | 11/2003 | Ehnholm et al. | |
| 2005/0197583 A1 * | 9/2005 | Chance | 600/476 |
| 2005/0201937 A1 * | 9/2005 | Hellerstein | 424/9.2 |
| 2006/0020204 A1 * | 1/2006 | Serra et al. | 600/437 |
| 2009/0104123 A1 * | 4/2009 | Yang et al. | 424/9.3 |

FOREIGN PATENT DOCUMENTS

| | | |
|---|---|---|
| DE | 198 44 767 A1 | 4/2000 |
| WO | WO 95 21582 A | 8/1995 |
| WO | WO 98 22022 A | 5/1998 |

\* cited by examiner

*Primary Examiner* — Tse Chen
*Assistant Examiner* — Baisakhi Roy

(57) ABSTRACT

The subject invention pertains to a method and apparatus for positioning a biopsy needle relative to lesion tissue. A desired imaging modality can be used to image the human or animal tissue to locate lesion tissue. Such an image can be referred to as a diagnostic image. In a specific embodiment, magnetic resonance imaging (MRI) can be utilized to locate one or more lesions in a human breast. An interventional instrument, such as a means for effecting a biopsy of the lesion tissue can then be positioned proximate the lesion tissue based of the location information about the location of the lesion tissue obtained from the diagnostic image. The desired imaging modality can then be used to confirm the accuracy of the position of the means for effecting a biopsy with respect to the lesion. In a specific embodiment, MRI can be utilized to confirm the accuracy of the position of a biopsy needle. In alternative embodiments, other imaging modalities, such as computer tomography (CT), can be used and/or tissue in other parts of the human or animal body can be imaged.

37 Claims, No Drawings

METHOD AND APPARATUS FOR POSITIONING A BIOPSY NEEDLE

CROSS-REFERENCE TO RELATED APPLICATION

The present application claims the benefit of U.S. provisional patent application Ser. No. 60/600,190, filed Aug. 6, 2004, which is hereby incorporated by reference herein in its entirety, including any figures, tables, or drawings.

BACKGROUND OF THE INVENTION

The present invention relates to the field of imaging and biopsy, and more particularly without limitations, to the field of Magnetic Resonance Imaging (MRI) of breast lesions and breast biopsy.

Prior art techniques for imaging and identifying the location of the breast lesions involves the introduction of a contrast agent that, due to the differences between the normal breast tissue and lesion tissue, can enable the detections of the lesion tissue under MRI. Systems can be utilized that incorporate fiducial markers, which can also appear in the MRI image. The fiducial markers can be positioned on a biopsy device such that the location of the lesion tissue relative to the biopsy device can be determined from a diagnostic MRI image taken of the breast held in a biopsy device. Positioning of a biopsy needle relative to the lesion tissue can then be accomplished by positioning the needle with respect to the biopsy device, where the position of the biopsy device relative to the lesion tissue is known from the diagnostic image.

Prior art techniques involve manually calculating the position of the lesion relative to the biopsy device, based on the knowledge of the fiducial markers in the MRI image showing the lesion, in order to assist in locating a needle to take a biopsy of the lesion. After such calculation, the biopsy needle is inserted to the lesion provided by the manual calculations in order to position the biopsy needle in position with respect to the lesion tissue. The desired position of the biopsy needle can allow determination of a point of entry into the tissue, an angle of entry into the tissue, and a depth of entry into the tissue. Once the biopsy needle is inserted, another MRI image can be taken to confirm the accuracy of the placement of the biopsy needle.

However, the process of manually calculating the position of the lesion, based on the knowledge of the fiducial markers in the MRI image showing the lesion, is time-consuming. Due to the time needed to manually calculate the location of the lesion, based on the relative position of the lesion with respect to the fiducial markers in the diagnostic MRI image, typically the contrast agent no longer allows identification of the lesion tissue by the time the interventional MRI image is taken to confirm the location of the biopsy needle. Therefore, the accuracy of the biopsy needle placement depends on the accuracy of the manual calculations based on the relative position of the lesion with respect to the fiducial marks in the diagnostic image. Due to the movement of the breast with respect to the biopsy device, during the period of time between taking the original diagnostic MRI image to image the lesion and taking the latter interventional MRI image confirming the location of the biopsy needle, the relative position of the lesion tissue with respect to the fiducial markers and, therefore, the relative position of the lesion tissue with respect to the biopsy device in the interventional MRI image is not known with great accuracy. In particular, factors such as inaccuracies of the manual calculations and movement of the breast with respect to the fiducial marker can negatively impact the accuracy of the positioning of the biopsy needle relative to the lesion tissue.

Accordingly, there exists a need in the art for a system and method that can allow more accurate placement of the biopsy needle relative to lesion tissue. Additionally, there is a need in the art for a system and method that can allow placement of the biopsy needle while the contrast agent still allows identification of the lesion tissue during the taking of the interventional MRI image. In this way, a more accurate placement of the biopsy needle relative to the lesion tissue can be achieved.

DETAILED DISCLOSURE OF THE INVENTION

The subject invention pertains to a method and apparatus for positioning a biopsy needle relative to lesion tissue. A desired imaging modality can be used to image the human or animal tissue to locate lesion tissue. Such an image can be referred to as a diagnostic image. In a specific embodiment, magnetic resonance imaging (MRI) can be utilized to locate one or more lesions in a human breast. An interventional instrument, such as a means for effecting a biopsy of the lesion tissue can then be positioned proximate the lesion tissue based of the location information about the location of the lesion tissue obtained from the diagnostic image. The desired imaging modality can then be used to confirm the accuracy of the position of the means for effecting a biopsy with respect to the lesion. In a specific embodiment, MRI can be utilized to confirm the accuracy of the position of a biopsy needle. In alternative embodiments, other imaging modalities, such as computer tomography (CT), can be used and/or tissue in other parts of the human or animal body can be imaged.

The subject invention can incorporate a combination of hardware, such as a biopsy device having integrated fiducial markers, and planning software, which makes use of fiducial markers for automatic/, semi-automatic/, and/or manual calibration of the position of a biopsy needle. A desired imaging modality can be used to image the fiducial markers that are used to calibrate the device. Such an image can be referred to as a calibration image and can be, for example, a DICOM image series. The subject invention can provide means for adjustments of the hardware based on the interactive analysis of images of the tissue.

The biopsy device can have a means for securely holding the tissue to be imaged such that the relative position of the tissue to be imaged to the means for holding the tissue is substantially maintained, and, in a specific embodiment maintained within a one cm accuracy. An image acquired under these conditions can be referred to as an interventional image. The biopsy device can also include a means for allowing the insertion point of a biopsy needle to be confirmed. Such a means can be, for example, a grid structured to identify various entry points for a biopsy needle. The biopsy device can also incorporate a means for controlling the angle of the inserted biopsy needle, such as a post and pillar.

In a specific embodiment, the hardware can include a biopsy device having fiducial markers for detection under the imaging modality, such as MRI. In an embodiment, a GD-water solution is placed in a hollow cavity, which is placed on the biopsy device in order to create fiducial markers. In another embodiment, a gelatin with Gd can be used to create fiducial markers.

The fiducial markers can have certain symmetries and/or asymmetries, which can allow the identification of the fiducial marker(s) in the image to provide information as to the position, and, optionally, the orientation of the fiducial marker(s). Accordingly, it is possible to utilize a single fiducial marker, where the orientation of the imaging apparatus with respect to the fiducial marker is known, such that the presence of the single fiducial marker in the image allows the determination of the location of any identified tissue in the image with respect to the biopsy device incorporating the single fiducial marker. In additional embodiments, two or more fiducial markers can be incorporated into the biopsy device. In an embodiment, two fiducial markers can be utilized. In a specific embodiment, three non-colinear fiducial markers are utilized. In this embodiment, each of the fiducial markers can be symmetrical in three dimensions. In a specific embodiment, a breast biopsy device in accordance with the subject invention can provide medial lateral stabilization of the breast tissue. In this way, the image can be from a sagittal acquisition. Of course, other acquisitions can be utilized.

In specific embodiments, the subject biopsy device can incorporate a means for guiding the biopsy needle into the tissue to be biopsied. The location of the fiducial markers on the biopsy device can also be used to allow the device software to recognize which biopsy device is being used during the imaging. This recognition of which biopsy device is being used can allow the subject invention to calibrate appropriately and to give targeting coordinates consistent with the structure of the biopsy device. In specific embodiments, the targeting coordinates can be consistent with a grid or post and pillar targeting structures. The subject invention can also provide targeting coordinates consistent with the DICOM coordinate system. In addition to fully automatic calibration, the subject invention can also allow for a semi-automatic or fully manual calibration procedure.

In an embodiment, the subject invention involves a method of positioning an interventional instrument within a portion of human or animal tissue. The method includes positioning a portion of human or animal tissue in a biopsy device, where the tissue has some normal tissue and some lesion tissue, where the tissue is maintained in a substantially fixed position with respect to the biopsy device, and where the biopsy device incorporates at least one fiducial marker which can be identified under an imaging modality. The tissue is imaged via the imaging modality to produce a calibration image of the tissue, where the calibration image shows the position of the at least one fiducial marker. The tissue is imaged via the imaging modality to produce a diagnostic image of the tissue, where the diagnostic image shows the position of the lesion tissue. The interventional instrument, such as a biopsy device, can then be calibrated with respect to the at least one fiducial marker and the location of the lesion tissue with respect to the biopsy device can then be calculated. The biopsy needle can then be positioned in the tissue such that the biopsy needle is in a desired position with respect to the lesion tissue based on the calculated location of the lesion tissue. The tissue can then be imaged via the imaging modality to produce an interventional image of the tissue with the biopsy needle positioned in the tissue, where the lesion tissue can be differentiated from the normal tissue, where the interventional image shows the position of the biopsy needle and the lesion tissue. The position of the biopsy needle can then be adjusted, if needed, based on the relative position of the biopsy needle and the lesion tissue.

With respect to some tissues it may be preferable to utilize a contrast agent. In an embodiment, a contrast agent can be introduced into the tissue, where the difference between the transport characteristics of the contrast agent in normal tissue and the transport characteristics of the contrast agent in lesion tissue allows differentiation of the lesion tissue from the normal tissue in an image taken via the imaging modality. The diagnostic image can be produced after the contrast agent allows differentiation of the lesion tissue from the normal tissue, and the interventional image is produced while the contrast agent still allows differentiation of the lesion tissue from the normal tissue. In an embodiment, the calculation of the location of the lesion tissue is automatic so as to speed up the calculation and allow the interventional image to be taken while the contrast agent still allows differentiation of the lesion tissue from the normal tissue. In an embodiment, this calculation can be implemented by placing the cursor on the lesion and, as the position of the fiducial marker is known so is the position with respect to the fiducial marker. The calibration image and diagnostic image can be one in the same, for example if the image provides adequate resolution.

In an embodiment, software can retrieve or receive diagnostic images or calibration scans, and interventional images or interventional scans, and can perform one or more of the following: prepare image data for easy access (for example create volumes and/or time series); provide hangings for presenting interventional and calibration (and optionally diagnostic) image series; provide a given workflow for calibration and interventional targeting of lesions; provide coordinates and estimate accuracies for lesion assessment; offer means for documentation of biopsy planning; and provide automatically prepared hangings of both interventional and diagnostic (including, but not restricted to prior) studies. In addition, the subject invention, via for example software, can include algorithms for automatic, semiautomatic, and/or manual calibration of the subject device based on the signal of the fiducial markers. These algorithms can include automatic detection of fiducial marker location, fiducial marker size, and fiducial marker orientation.

The software can retrieve or receive both diagnostic and interventional calibration scans and can perform one or more of the following: automatically, semiautomatically, or manually calibrate the biopsy device; prepare the diagnostic scans and provide a user with a hanging to analyze the diagnostic data for lesion detection; automatically synchronize the diagnostic and interventional datasets; and allow the user to localize the lesion in the diagnostic data and due to synchronization provide automatically the target coordinates for intervention and updates a graphical representation of the biopsy device. An additional diagnostic scan can be performed in the same exam prior to the intervention, for example, when there is no prior diagnostic exam electronically available. The biopsy device can be used for the diagnostic scan and can, optionally, compress the breast a little.

The subject hanging protocols can be applied after preprocessing of a single study, when additional image series are added to a study, and/or when opening two or more studies. In the latter case, the cross study application of hanging protocols is being checked and corresponding hangings created, if available, for the creation of customized hanging protocols. The subject invention can allow for the creation of hangings for comparing current and prior exams.

The subject invention pertains to a tool for organizing the workflow of a radiological image reading environment. In an embodiment, the subject invention can incorporate a means for user and worklist management. In a specific embodiment, the means for the user and worklist management can define different worklists which include Tasks depending on their contained image sets and matching descriptors. Such a worklist may, for example, contain breast MRI exams and/or digital mammography.

A task can include one or more of the following: a set of hanging protocols, preprocessed data, a history file and user annotations, result images and reports.

A user can belong to at least one worklist which is accessible after log in. In an embodiment, cluster technology can perform automatic pre-fetching of image data that forwards certain types of image data to selected clients. The subject invention can perform central preprocessing of incoming image data on server(s). In an embodiment, one combined workspace can be maintained on all clients where users can log in any system.

In addition, configurable automatic preprocessing of DICOM studies for generation of image sets and, optionally, motion correction, including volumes and time series, with related image content can use, for example, preprocessing rules and/or DICOM tags. Moreover, hanging protocols can be used to describe the way the image data is presented in different viewers on, for example, one, two, or more monitors. The subject hanging protocols can be different from the DICOM hanging protocols so as to use much broader descriptors than DICOM tags only. In an embodiment, the geometric information which is available after preprocessing can be incorporated into the subject hanging protocols. The hanging protocols can be defined by layouts and descriptors. Sorting and partitioning rules based on, for example, DICOM tags can be utilized.

Applying a Hanging Protocol can create a persistant hanging, which consists of the prepared image sets and the way the image data is presented. In addition, a history of changes to this hanging and optionally annotations can be stored persistantly. This allows archival or transfer of these persistant hangings to other worklists or users (e.g. for clinical demonstration purposes). For example, annotations can be added to the image sets, such as text, geometrical figures, distance measurements, and arrows. These additions can be documented and saved.

Inspectors are windows on the work area that present images, image sets, and means to interact with them. These inspectors can include, but are not restricted to, an alternator, a MIP inspector, a DynaLOC inspector, DynaFlow inspector, and a MPR inspector. The alternator is a basic 2D viewer for image sets that can stack through images of a volume dataset, window-level, loop over time (for 4d-datasets), perform zooming, perform subtraction of images (for 4d datasets only), reformat image orientation (for 3d volumes), overlay of colorized functional overlays (for 4d datasets only), and provide point selection and annotation.

The MIP inspector can provide a 3D projection display of rotation, subtraction (4d only), subvolume, color overlay (DynaMIP), point selection, annotation, and loop over time (4d only). The DynaLOC inspector can connect to calibration images to show a biopsy device, where if calibrated, can move the device according to selected point in connected inspector, e.g. representing the lesion and can compute coordinates and needle depth for intervention. The DynaFlow inspector can extract time intensity curves for selected point in connected inspector, compute enhancement curves for diagnostic purposes, compute parametric overlays on connected inspectors based on different algorithms for encoding the shape of the time intensity curve in different colors, and compute statistics of parametric overlays in a defined region of interest of a connected inspector. The MPR inspector (multiplanar reformations) can show three orthogonal reformations of the dataset. In a specific embodiment, the currently selected point can be visible in all views.

The layouts can contain configuration of placement of inspectors and can provide a possibility to synchronize parameters of inspectors, e.g. selected point, window-leveling, zooming, selected time, subtraction mode, and orientation. This means, that the synchronized inspector groups show their image content using the same parameters. The descriptors can be based DICOM tags or, contents of DICOM tags and other image properties, such as 3d, 4d, etc. These descriptors can be used for automatically placing the matching images into corresponding inspectors (viewers) in a layout of a hanging protocol and can forward incoming data (Studies) to corresponding worklist. The descriptors can include variants which are logically combined, where at least one of the variants must match such that the descriptors match and each variant contains one or more criteria which are logically combined. These criteria can be DICOM tags or meta information.

The layouts can contain configurations of specialized inspectors that, for example, show parametric overlays on the original images or show 3D visualizations.

In a specific embodiment, the hanging protocols can be analyzed for applicability both after preprocessing of a single study, when additional preprocessed image series for the same study are added, and when opening two or more studies. In the latter case, the cross study application of hanging protocols can be checked and corresponding hangings created, if available. This is probably a new and unique way for the creation of customized hanging protocols. Especially, this includes the possibility to create hangings for comparing current and prior exams.

Embodiments of the subject invention also relate to a method and apparatus for generating structured reports. One or more images can be provided to an embodiment of the subject invention. These images can be produced by any of a variety of imaging modalities, such as magnetic resonance imaging (MRI) and computer tomography (CT). The images can be provided by the user and/or retrieved by an embodiment of the subject invention. The images can have footers, headers, and/or have information accompanying the images. Such information can include, but is not limited to, the patient's name, and/or other patient information, the date of the image acquisition, the type of image acquisition, and other information known to those skilled in the art. In a specific embodiment, the images can have information in accordance with the DICOM Standard accompanying the images.

Various embodiments of the subject invention can create report structures that are useful for providing information regarding the images, such as whether a lesion exists, how big the lesion is, where the lesion is located, how the lesion is responding to treatment over time, and how fast the lesion is growing or shrinking. One or more of the report structures can then be offered to a user, or a report structure can be selected for a user, based on information from the images and/or information accompanying the images.

In an embodiment, the method can allow trained users or administrators to create their own templates for structured reports. The structured reports can be tailored to specific disease oriented questions or certain types and sets of exams. Embodiments of the subject software can provide means to automatically match predefined report types to a given study and provide tools for generating different kinds of report information such as findings, measurements, and capture images, and can allow the same to be generated either interactively by the user, or semi- or fully automatically by the software. This information can be automatically available in the report in a structured form. The user can also additionally add more information to the report, such as written text or classifications that can be added through a user interface based on the predefined sets of classification categories. One example of such a structured report configuration is the ACR BIRADS atlas.

Embodiments of the subject invention can be implemented via software. The software can incorporate one or more of many subparts, such as those described below. Software for implementing embodiments of the subject invention can incorporate a structured report engine, for example as a software component, which can provide tools, such as a structured report editor for the application to support the configuration and/or setup of different structured report types for the administrator of the software. The structured report engine can also provide tools to be used by the user to generate structured reports for given exams such as one or more of the following: report tool, print tool, result generation tools, and finding folders.

The structured report engine can include a structured report editor, which can include editors for the creation and management of structured report types. A structured report type can include typed concepts that are defined in SR Lexicons, where SR stands for structured report. These typed concepts can for example be enumerations, composites of typed concepts, scalars or bitmaps. The structured report editor can also include a SR Lexicon editor to define the typed concepts, a report structure editor that defines the hierarchical structure of structured report types. The structured report editor can include an SR report property editor that, for example, can define inheritances between structured report types. For example, a generic report can be created that includes the patient name and/or other information. The SR report property editor can define an inheritance such that each report incorporates the information in the generic report.

One example of a SR Lexicon in accordance with the subject invention is the language and definitions contained in the ACR BIRADS atlas, the ACR BIRADS Lexicon. The structured report editor can also include the report structure editor that allows defining sections, which may include any number of typed concepts, and the order of those sections. The administrator of the software can use the structured report editor to setup any kind of structured report types based on appropriate SR Lexicons, which the administrator can also define. The administrator can also predefine the order in which the user will see the content of reports of the corresponding structured report type.

The user can use the application to create structured reports for selected exams. Finding identification tools can be utilized to locate and mark findings, such as a lesion, in the image data. These finding identification tools can be either some type of interactive annotations that the user can place near findings that he identifies manually, or the finding identification tools can be automatic identification tools that identify findings fully automatically in a preprocessing step, such as with computer aided detection.

A finding folder can be made available for each identified finding and can be represented in the application's user interface. The finding folder can contain information related to the identified finding. A finding can be related to some location in one of the image datasets of the exam that shows some structure that the user wants to report. Examples of findings include a lesion or some other finding as described in the ACR BIRADS lexicon. The finding folder can include one or more finding markers that document the location of the finding in the image data. This can be, for example, presentation states referencing the position of the marker, a reference to the image data and a capture of the corresponding images with an overlay showing the marker position and identification.

In an embodiment, the application can provide result generation tools that the user can use to extract and document any kind of information to describe the finding. Examples of result generation tools include image analysis tools such as enhancement curves, volumes, processed images (parametric maps, MIPs, MPRs) or statistics. There can also be annotation tools to create capture images with or without textual or graphical annotations and measurements.

An embodiment can incorporate image analysis tools that can be report specific tools, such as Breast MR specific tools to support the generation of information as defined in the ACR BIRADS Lexicon. For example, tools to determine the distance to nipple/chest wall/skin, the lesion location/volume, enhancement composition, and/or the worst looking curve.

In an embodiment, the result generation tools can also be automatic result generation tools that need restricted or no user interaction. The application can provide a SR generation mechanism that can include a SR filling mechanism and a SR identification mechanism. The SR identification mechanism can define the number and structured report types of reports generated and available for the user and a certain study. The SR identification mechanism can provide a user interface and allow the user to select reports from the list of predefined structured report types. The SR identification mechanism can also be an Automatic SR identification mechanism, such as a descriptor based SR identification mechanism that allows restricting the availability of certain structured report types based on the matching of image data in the study to predefined descriptors. The SR generation mechanism can also include a SR filling mechanism which fills generated structured reports with information generated from the typed results available in the finding folders. This mechanism can be an automatic SR filling mechanism such that the structured reports automatically show up the typed results in the predefined sections of the structured report type.

In an embodiment, the application can include a report tool that provides the user with a user interface to edit the structured reports. The typed results can appear in the corresponding sections of the structured report as a result of the automatic SR filling mechanism. The typed concepts included in the structured report can be represented with user interfaces that allow the user to select from predefined values, such as enumerations, and composites and to edit any additional information that is required, such as text or other user input. The SR generation mechanism can include a SR Parser that allows exporting the structured reports in different formats. This can be paper print or DICOM SR. The report tool can allow the user to send the structured report to a printer, PACS, and/or email-addresses.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. A method of positioning an interventional instrument relative to lesion tissue in normal human or animal tissue, comprising:

positioning a portion of the human or animal tissue in a biopsy device which includes an interventional instrument for biopsying the lesion tissue, wherein the tissue has some of the normal tissue and some of the lesion tissue, wherein the tissue is maintained in a fixed position with respect to the biopsy device, wherein the biopsy device comprises at least one fiducial marker which can be identified under at least a first imaging modality;

imaging the tissue via the first imaging modality to produce a calibration image of the tissue, wherein the calibration image shows the position of the at least one fiducial marker;

introducing a contrast agent into the tissue, wherein a difference between transport characteristics of the contrast agent in normal tissue and the transport characteristics of the contrast agent in the lesion tissue differentiates the lesion tissue from the normal tissue;

calibrating the biopsy device with respect to the at least one fiducial marker using the calibration image;

imaging the tissue via the first or another imaging modality to produce a diagnostic image of the tissue after the contrast agent has differentiated the lesion tissue from the normal tissue, such that the diagnostic image shows the lesion tissue;

with a software programmed device, automatically calculating from the calibration and diagnostic images, a location of the lesion tissue with respect to the biopsy device;

positioning the interventional instrument in the tissue such that the interventional instrument is in a desired position with respect to the lesion tissue based on the calculated location of the lesion tissue;

while the contrast agent is still differentiating the lesion tissue from the normal tissue, imaging the tissue to produce an interventional image of the tissue and the interventional instrument positioned in the tissue in which the lesion tissue is still differentiated from the normal tissue by the contrast agent, wherein the interventional image shows a relative position of the interventional instrument and the contrast agent differentiated lesion tissue;

adjusting the position of the interventional instrument, if needed, based on the relative position of the interventional instrument and the lesion tissue.

2. The method according to claim 1, wherein the tissue is maintained in the fixed position with respect to the biopsy device until after adjusting the position of the biopsy needle, if needed.

3. The method according to claim 1, wherein the portion of human or animal tissue is a human breast.

4. The method according to claim 1, wherein the biopsy device comprises two fiducial markers.

5. The method according to claim 1, wherein the biopsy device comprises at least three fiducial markers, wherein at least three of the at least three fiducial marker are non-colinear.

6. The method according to claim 1, wherein the interventional device includes a biopsy needle and the biopsy device comprises a plurality of openings and further including inserting the biopsy needle through one of the openings into the tissue.

7. The method according to claim 6, further comprising: automatically calculating a location at which the biopsy needle is to be positioned to enter the tissue, and a depth into the tissue which the biopsy needle is to be inserted, in order to position the biopsy needle in the lesion tissue.

8. The method according to claim 7, further comprising: selecting an angle with respect to the tissue at which the biopsy needle is to be inserted into the tissue.

9. The method according to claim 7, further comprising: overlaying a needle path of the biopsy needle onto the images.

10. The method according to claim 7, further comprising: computing and documenting coordinates of the lesion tissue and the interventional image onto a printable medium.

11. The method according to claim 10, further comprising: computing and storing the coordinates of the lesion tissue and the interventional image into a PACS system.

12. The method according to claim 1, wherein the diagnostic image is of a higher resolution than the interventional image.

13. The method according to claim 1, further including: targeting more than one lesion using the calibration.

14. The method according to claim 1, further comprising: automatically creating a volume image when the calibration and diagnostic images and/or information accompanying the calibration and diagnostic images indicates the calibration and diagnostic images are images of slices of a volume; and incorporating the volume image in a report.

15. The method according to claim 1, further comprising: selecting a report structure from a plurality of report structures based on information from one or more of the images and/or information accompanying the one or more images, wherein the selected report structure is selected based on the analysis of the one or more images, wherein the selected report structure is useful for providing information regarding biopsying the lesion tissue; and producing a report in the selected report structure.

16. The method according to claim 15, wherein selecting a report structure comprises:

providing the user at least two report structures from the plurality of report structures to choose from and the user selecting a report structure.

17. The method according to claim 15, wherein the imaging modality is magnetic resonance imaging (MRI).

18. The method according to claim 17, further comprising: providing the user one or more identification tools for identifying findings in the one or more images.

19. The method according to claim 17, wherein the images are breast images.

20. The method according to claim 15, wherein the imaging modality is computer tomography (CT) imaging.

21. The method according to claim 15, wherein the information from the one or more images and/or information accompanying the one or more images comprises information selected from the group consisting of: image modality, image spatial resolution, image protocol, number of images, and DICOM tags.

22. The method according to claim 15, wherein selecting a report structure from a plurality of report structures comprises selecting a report structure from a plurality of predetermined report structures.

23. The method according to claim 15, further comprising: creating an additional report structure; and including the additional report structure in the plurality of report structures.

24. The method according to claim 15, further comprising; producing a generic report providing standard information, wherein the standard information is incorporated into the report.

25. The method according to claim 15, further comprising: automatically applying one or more built in identification tools for identifying findings; and incorporating any findings from the one or more built in identification tools into the report.

26. The method according to claim 25, wherein the one or more built in identification tools comprises a lesion identification tool.

27. The method according to claim 15, wherein producing a report in the selected report structure comprises:
   selecting a report tool which results in production of a report in the selected report structure.

28. The method according to claim 15, further comprising:
   providing the user one or more image analysis tools for analyzing the lesion tissue in the diagnostic image.

29. The method according to claim 15, wherein selecting a report structure from a plurality of report structures comprises automatically selecting a report structure from the plurality of report structures.

30. The method according to claim 1, further comprising:
   storing the diagnostic image, coordinates of the lesion tissue, and documentation of biopsy planning in a finding folder;
   selecting one of a plurality of report structures; and
   producing a report in the selected report structure incorporating contents of the finding folder.

31. The method according to claim 1, wherein the interventional instrument is a biopsy needle.

32. The method according to claim 1, further including, with the software programmed device:
   displaying the diagnostic images with the differentiated lesion tissue;
   providing coordinates of the lesion tissue;
   displaying a graphical representation of the biopsy device with the diagnostic image; and
   updating the display of the graphical representation of the biopsy device when the interventional instrument is adjusted.

33. The method according to claim 1, further including, with the software programmed device:
   preparing a report including the diagnostic image, coordinates of the lesion tissue, estimates of accuracy of lesion tissue assessments, and documentation of biopsy planning.

34. An interventional method comprising:
   positioning and fixing human or animal tissue which includes normal tissue and lesion tissue in a biopsy device which has a tissue fixing portion, a portion for defining a trajectory of a biopsy needle, and a plurality of fiducial markers;
   imaging the tissue in the tissue fixing portion to generate a high resolution diagnostic image of the tissue showing at least the normal tissue, the lesion tissue differentiated with a contrast agent, and the plurality of fiducial markers;
   with a software programmed device, calculating an entry location of the biopsy needle into the tissue, an angle of the biopsy needle and a depth of biopsy need insertion which define a trajectory which positions the biopsy needle in a preselected position relative to the lesion tissue;
   inserting the biopsy needle along the trajectory to the preselected position;
   while the lesion tissue is still differentiated with the contrast agent, generating one or more interventional images, the interventional image being lower in resolution than the diagnostic image;
   displaying the diagnostic image and a graphical representation of the biopsy device;
   updating the graphical representation as the biopsy needle is moved;
   when one of the interventional images show the biopsy needle to be in the preselected position, biopsying the lesion tissue;
   selecting one of a plurality of predefined report formats;
   generating a report in the selected format which includes the diagnostic image, at least one of the one or more interventional images, information about the lesion tissue, and other biopsy information.

35. The method according to claim 34, wherein the high resolution diagnostic image is generated by magnetic resonance imaging (MRI).

36. The method according to claim 34, wherein the high resolution diagnostic image is generated by computer tomography (CT) imaging.

37. An interventional method comprising:
   positioning a region of a patient which has normal tissue and lesion tissue in a biopsy device which includes a tissue fixing portion, a portion for fixing a trajectory of a biopsy needle, and fiducial markers;
   imaging the patient region to generate a diagnostic image which shows a location of the lesion tissue;
   imaging the biopsy device and the patient region to generate a calibration image which shows locations of the fiducial markers;
   with a software programmed device, calculating an entry location of the biopsy needle, a trajectory of the biopsy needle, and a depth of insertion;
   inserting the biopsy needle along the trajectory;
   imaging the patient region and the biopsy needle to generate an interventional image which shows a position of the biopsy needle and the lesion tissue;
   with the software programmed device, calculating an adjustment to at least one of the trajectory and insertion depth based on the intervention image;
   injecting a contrast agent which differentiates the lesion tissue from the normal tissue into the patient such that the contrast agent differentiates the lesion from the normal tissue in at least the diagnostic and interventional images;
   with the software programmed device, synchronizing the diagnostic and interventional images, selecting images for display to a clinician performing the biopsy, selecting one or more structured report formats and suggesting the one or more report formats to the clinician for selection, retrieving patient data to populate a selected structured report format, and automatically or semi-automatically populating the selected structured report formats with the patient data, selected diagnostic and interventional images, and clinician created findings and diagnoses.

* * * * *